United States Patent [19]

Ogura et al.

[11] Patent Number: 5,595,180

[45] Date of Patent: Jan. 21, 1997

[54] METHOD AND APPARATUS FOR WINDING CUFF IN BLOOD PRESSURE MEASUREMENT

[75] Inventors: Toshihiko Ogura, Inuyama; Akihiro Yokozeki; Chikao Harada, both of Komaki, all of Japan

[73] Assignee: Colin Corporation, Aichi-ken, Japan

[21] Appl. No.: 288,080

[22] Filed: Aug. 10, 1994

[51] Int. Cl.$^6$ ..................................................... A61B 5/02
[52] U.S. Cl. ........................................... 128/686; 128/679
[58] Field of Search .................................. 128/677–681, 128/682–685, 686; 340/815.45

[56] References Cited

U.S. PATENT DOCUMENTS

| | | | |
|---|---|---|---|
| 3,935,984 | 2/1976 | Lichowsky et al. | |
| 4,003,370 | 1/1977 | Emil et al. | |
| 4,274,424 | 6/1981 | Kimura et al. | |
| 4,429,699 | 2/1984 | Hatschek | 128/686 X |
| 4,660,567 | 8/1987 | Kaneko et al. | 128/680 X |
| 4,667,685 | 5/1987 | Fine | |
| 4,812,814 | 3/1989 | Elliott | 340/815.45 X |
| 5,172,697 | 12/1992 | Koven et al. | 128/677 X |

FOREIGN PATENT DOCUMENTS

| | | |
|---|---|---|
| 407693 | 1/1991 | European Pat. Off. |
| 3029473 | 3/1982 | Germany. |
| 2141344 | 12/1984 | United Kingdom. |
| 2257529 | 1/1993 | United Kingdom. |

*Primary Examiner*—Angela D. Sykes
*Assistant Examiner*—Ryan Carter
*Attorney, Agent, or Firm*—Oliff & Berridge

[57] ABSTRACT

A method and apparatus for winding a cuff having an inflatable chamber around a body portion of a living subject, in measuring a blood pressure of the subject, the method including the steps of positioning the cuff and the body portion of the subject relative to each other such that the cuff surrounds the body portion, supplying a predetermined amount of gas into the chamber of the cuff to hold the gas in the chamber, and fastening the cuff after increasing a tension of the cuff till a gas pressure in the chamber of the cuff surrounding the body portion reaches a reference value. A cuff winding apparatus includes a gas supplying device which supplies a predetermined amount of gas into the chamber of the cuff to hold the gas in the chamber, a pressure sensor which detects a gas pressure in the chamber of the cuff, a judging device for judging whether the pressure of the chamber detected by the pressure sensor has reached a reference value, and a driving device which increases a tension of the cuff to reduce a diameter of the cuff surrounding the body portion of the subject, the driving device holding the diameter of the cuff when the judging device makes a positive judgment.

9 Claims, 8 Drawing Sheets

METHOD AND APPARATUS FOR WINDING CUFF IN BLOOD PRESSURE MEASUREMENT

BACKGROUND OF THE INVENTION

1. Field of the Invention

The present invention relates to a method and an apparatus for winding a cuff having an inflatable chamber into which pressurized gas is to be supplied, around a body portion of a living subject, in measuring blood pressure of the subject.

2. Related Art Statement

When blood pressure of a living body or subject is measured, a cuff having an inflatable chamber into which pressurized gas is to be supplied, is wound around a body portion of the subject, to press arteries running in the body portion. The manner of winding of the cuff around the body portion influences the relationship between the gas pressure in the inflatable chamber of the cuff (hereinafter, referred to as the "cuff pressure" or "pressing pressure") and the state of pressing of the arteries in the body portion. That is, even at the same cuff pressure or pressing pressure, the state of pressing of the arteries in the body portion may change depending upon the manner of winding of the cuff around the body portion. Hence, it is widely recommended that a cuff be wound around a body portion in such a manner that two or three fingers can easily be inserted between the cuff and the body portion.

Meanwhile, a body portion of a living subject, such as an upper arm or a femur, very easily deforms. Thus, the winding of a cuff around the body portion needs the skill of a user such as a doctor or a nurse. Moreover, the relationship between cuff pressure and state of pressing of arteries in a body portion may change among individual subjects. The change of relationship results in lowering the accuracy of blood pressure (BP) measurements of the individual subjects.

In the case where a pulse wave is detected as a pressure oscillation produced in an inflatable chamber of a cuff in synchronism with heartbeat of a subject, the change of relationship influences the waveform of the pulse wave detected. In this respect, too, it is desirable that the cuff be wound around the body portion in an appropriate manner.

SUMMARY OF THE INVENTION

It is therefore an object of the present invention to provide a method and an apparatus for winding, in an appropriate manner, a cuff around a body portion of a living subject, in measuring blood pressure of the subject.

The above object has been achieved by the present invention. According to a first aspect of the present invention, there is provided a method of winding a cuff having an inflatable chamber around a body portion of a living subject, in measuring a blood pressure of the subject, comprising the steps of: positioning the cuff and the body portion of the subject relative to each other such that the cuff surrounds the body portion, supplying a predetermined amount of gas into the chamber of the cuff to hold the gas in the chamber, and fastening the cuff after increasing a tension of the cuff till a gas pressure in the chamber of the cuff surrounding the body portion reaches a reference value.

In the cuff winding method arranged as described above, the cuff into the inflatable chamber of which a predetermined amount of gas has been supplied is fastened after a tension of the cuff has been increased till a gas pressure in the chamber of the cuff surrounding the body portion of the subject reaches a reference value. Thus, the present cuff winding method ensures that the cuff is wound around subject's body portion such as an upper arm, in an appropriate manner, without needing the skill of a user such as a medical worker or a patient. Therefore, the present method effectively prevents the lowering of accuracy of a cuff-using blood pressure measurement resulting from an inappropriate cuff winding around subject's body portion.

According to a second aspect of the present invention, there is provided an apparatus for winding a cuff having an inflatable chamber around a body portion of a living subject, in measuring a blood pressure of the subject, the cuff and the body portion being positioned relative to each other such that the cuff surrounds the body portion, the apparatus comprising: a gas supplying device which supplies a predetermined amount of gas into the chamber of the cuff to hold the gas in the chamber; a pressure sensor which detects a gas pressure in the chamber of the cuff; judging means for judging whether the pressure of the chamber detected by the pressure sensor has reached a reference value; and a driving device which increases a tension of the cuff to reduce a diameter of the cuff surrounding the body portion of the subject, the driving device holding the diameter of the cuff when the judging means makes a positive judgment.

In the cuff winding apparatus constructed as described above, the driving device increases a tension of the cuff to reduce a diameter of the cuff surrounding the body portion of the subject, and the driving device holds the diameter of the cuff when the judging means makes a positive judgment, i.e., judges that the pressure of the chamber of the cuff detected by the pressure sensor has reached a reference value. Thus, the present cuff winding apparatus automatically winds, and holds, the cuff around subject's body portion in an appropriate manner, without needing the skill of a user. Therefore, the present apparatus effectively prevents the lowering of accuracy of a cuff-using blood pressure measurement resulting from an inappropriate cuff winding around subject's body portion.

According to a third aspect of the present invention, there is provided an apparatus for winding a cuff having an inflatable chamber around a body portion of a living subject, in measuring a blood pressure of the subject, the cuff and the body portion being positioned relative to each other such that the cuff surrounds the body portion, the apparatus comprising: a gas supplying device which supplies a predetermined amount of gas into the chamber of the cuff to hold the gas in the chamber; a pressure sensor which detects a gas pressure in the chamber of the cuff; and an indicating device which indicates that the pressure of the chamber detected by the pressure sensor has reached a reference value while a tension of the cuff surrounding the body portion of the subject is increased by a person.

In the cuff winding apparatus constructed as described above, the cuff into the inflatable chamber of which a predetermined amount of gas has been supplied is fastened after a tension of the cuff has been increased till the indicating device indicates that the pressure of the chamber of the cuff surrounding the body portion of the subject reaches a reference value. Thus, the present cuff winding apparatus ensures that, while observing the indicating device, a user winds, by his or her hands, the cuff around subject's body portion in an appropriate manner, without needing the skill of the person. Therefore, the present apparatus effectively prevents the lowering of accuracy of a cuff-using blood pressure measurement resulting from an inappropriate cuff winding around subject's body portion.

BRIEF DESCRIPTION OF THE ACCOMPANYING DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
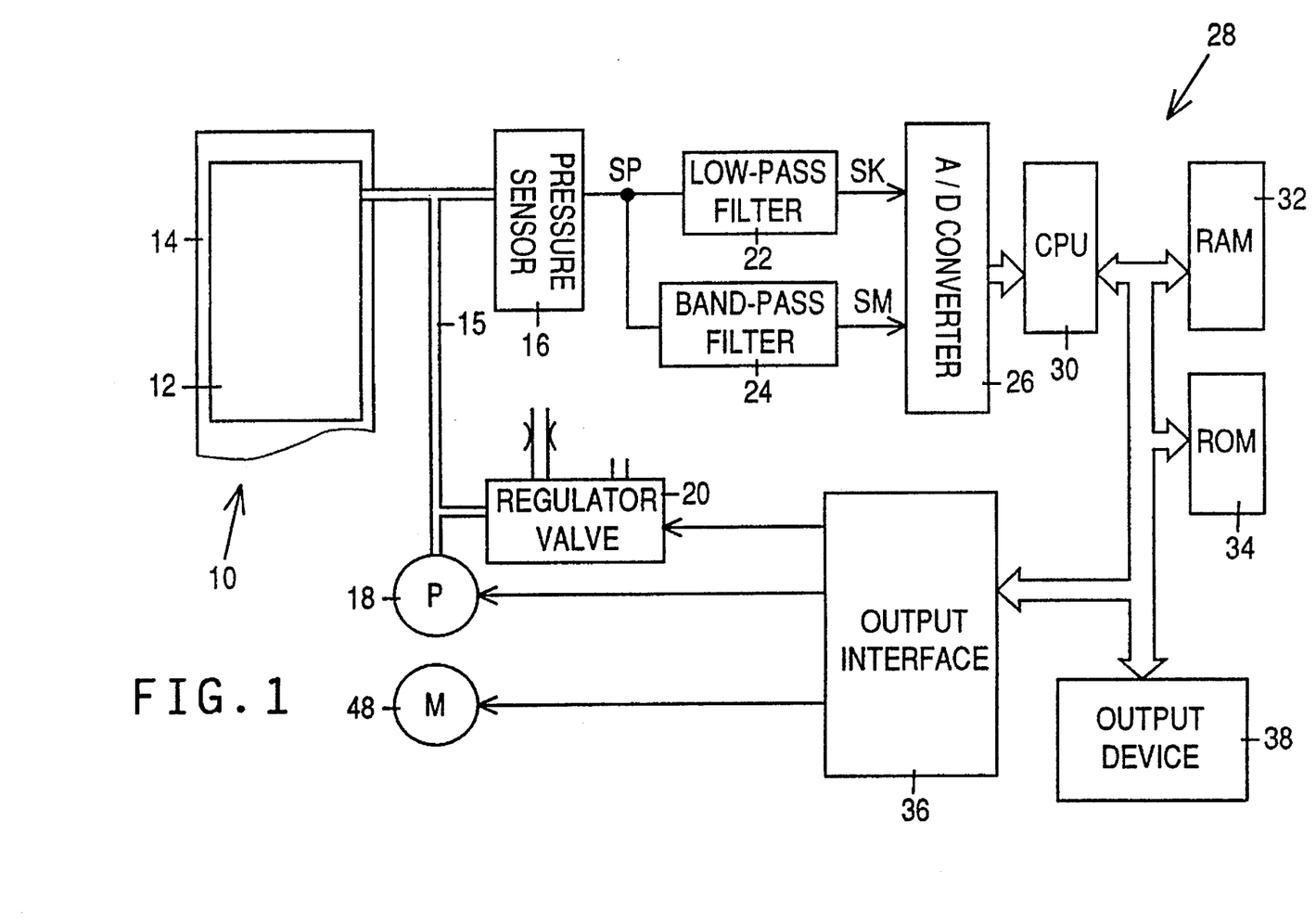
FIG. 1 is a diagrammatic view of an automatic blood pressure (BP) measuring apparatus embodying the present invention.

Referring first to FIG. 1, there is shown an oscillometric automatic blood pressure (BP) measuring apparatus to which the present invention is applied. Reference numeral 10 designates an inflatable cuff adapted to be wound around a body portion (e.g., upper arm) of a living subject (e.g., patient) so as to press the upper arm. The inflatable cuff 10 includes an elastically deformable bag 12 such as a rubber bag or a vinyl bag, and an elongate belt 14 such as a considerably hard cloth or a synthetic-resin sheet. The bag 12 defines an inflatable chamber therein. The inflatable bag 12 is fixed to one of opposite major surfaces of the belt 14 (hereinafter, the "one" surface will be referred to as the "inner" surface of the belt 14, and the other surface will be referred to as the "outer" surface of the same 14). The bag 12 of the cuff 10 is connected via piping 15 to a pressure sensor 16, an air pump 18, and an air-deflation regulator valve 20.

The pressure sensor 16 includes, for example, a semiconductor pressure sensing element (not shown) which detects an air pressure in the bag 12 of the cuff 10 ("cuff pressure" or "pressing pressure") and supplies a detection signal, SP, representing the detected pressure, to a low-pass filter 22 and a band-pass filter 24. The low-pass filter 22 permits only a DC (direct current) or static-pressure component of the detection signal SP to pass therethrough, thereby supplying a cuff-pressure signal, SK, representing the static cuff pressure, i.e., arm pressing pressure, Pk, to an analog to digital (A/D) converter 26.

The band-pass filter 24 permits only a 1 to 10 Hz frequency AC (alternating current) component of the detection signal SP to pass therethrough, thereby supplying a pulse wave signal, SM, representing a pulse wave of the subject, to the A/D converter 26. The pulse wave is a pressure oscillation produced in the bag 12 of the cuff 10 because of the pulsation of arteries in the upper arm in synchronism with heartbeat of the subject, while the cuff pressure Pk is changed within an appropriate pressure range. Thus, the pulse wave produced in the cuff 10 or bag 12 is obtained as the AC component (i.e., pulse wave signal SM) of the detection signal SP supplied from the pressure sensor 16. The A/D converter 26 has a time division multiplexer for time sharing of the two analog signals SK, SM and concurrently converts those analog signals to respective digital signals.

The present BP measuring apparatus also has an arithmetic control device 28 which is essentially constituted by a microcomputer including a central processing unit (CPU) 30, a random access memory (RAM) 32, a read only memory (ROM) 34, and an output interface 36. The CPU 30 receives the two digital signals SK, SM from the A/D converter 26, and processes those digital signals by utilizing the temporary-storage function of the RAM 32 and the control programs pre-stored in the ROM 34, so that the CPU 30 controls the respective operations of the air pump 18 and air-deflation regulator valve 20 through the output interface 36, and controls an output device 38. The output device 38 includes an image display (not shown) constituted by a number of light emitting elements (e.g., light emitting diodes). The image display displays measured blood pressure values in digits, and the waveform of detected pulse wave based on the pulse wave signal SM.

Figure 2:
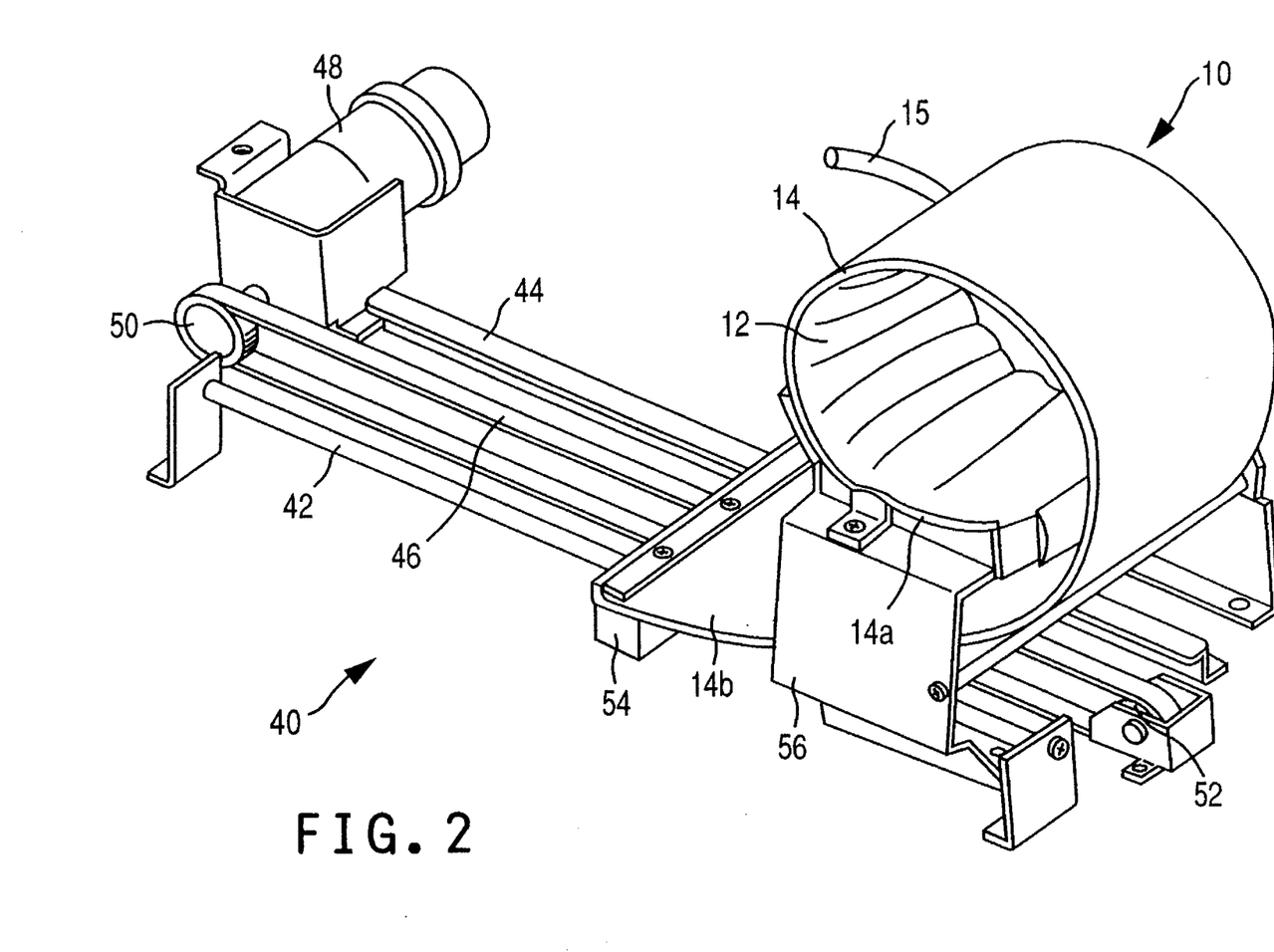
FIG. 2 is a perspective view of an automatic cuff winding device 40 of the apparatus of FIG. 1.

FIG. 2 shows an automatic cuff winding device 40 of the present BP measuring apparatus. The cuff winding device 40 includes a guide rod 42 and a guide rail 44 both of which are fixed to a frame member (not shown) so as to extend parallel to each other. An endless belt 46 is wound on one hand around a drive pulley 50 fixed to an output shaft of a drive motor 48 which is associated with reduction gears (not shown), and wound on the other hand around a driven pulley 52 rotatably supported by the frame member. The endless belt 46 is disposed between the guide rod 42 and guide rail 44 so as to extend parallel to those members 42, 44. A movable member 54 is fixed on one hand to an outer end 14b of the elongate belt 14 so bent as to have a generally cylindrical configuration, and is fixed on the other hand to an appropriate position of the drive belt 46, such that the movable member 54 is guided by the guide rod 42 and guide rail 44. The movable member 54 is fixed to an end portion of the outer surface of the belt 14 opposite to the inner surface thereof to which the inflatable bag 12 is fixed.

An inner end 14b of the cylindrically bent belt 14 is fixed to a support member 56, which is fixed to the frame member and covers the respective end portions of the guide rod 42 and guide rail 44. When the outer end 14b of the belt 14 is moved together with the movable member 54 as a result of operation or rotation of the drive motor 48, a diameter of winding of the belt 14 or cuff 10 around the upper arm is changed, that is, a length of contact of the cuff 10 with the upper arm is changed. The amount and direction of rotation of the drive motor 48 is controlled by the control device 28 or CPU 30.

Hereinafter there will be described the operation of the oscillometric BP measuring apparatus constructed as described above, by reference to the flow chart of FIGS. 3 and 4.

Figure 3:
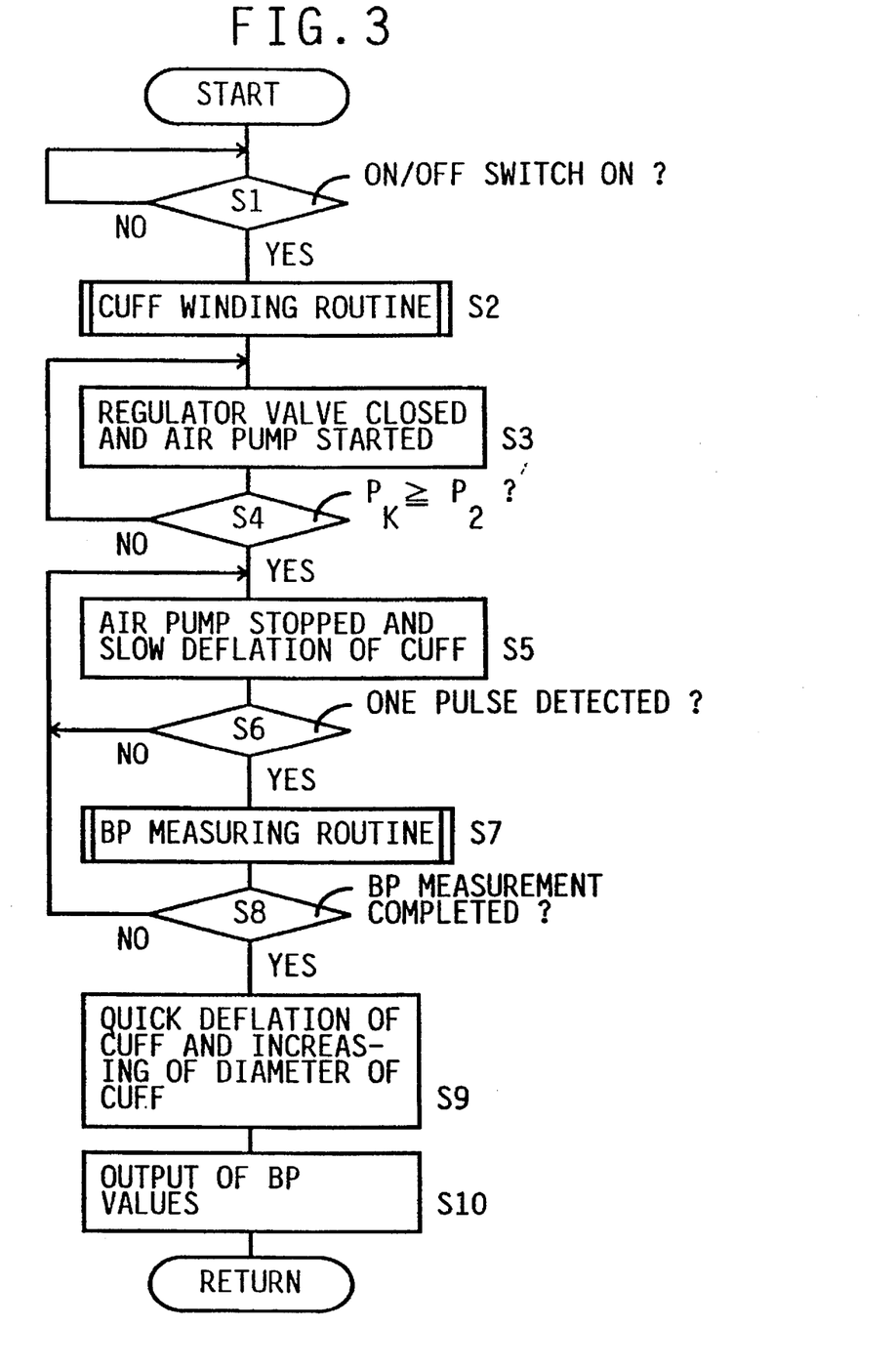
FIG. 3 is a flow chart representing a control program according to which the apparatus of FIG. 1 operates.

Initially, a body portion of a living subject, such as an upper arm of a patient, is inserted into the cylindrically bent belt 14 of the cuff 10. At Step S1, the CPU 30 of the control device 28 judges whether an ON/OFF switch (not shown) has been operated for starting the operation of the present apparatus, based on a START or a STOP signal supplied from the ON/OFF switch. If a negative judgment is made at Step S1, the CPU 30 waits for receiving the START signal from the ON/OFF switch. Meanwhile, if a positive judgment is made at Step S1, the control of the CPU 30 proceeds with Step S2, i.e., cuff winding routine.

Figure 4:
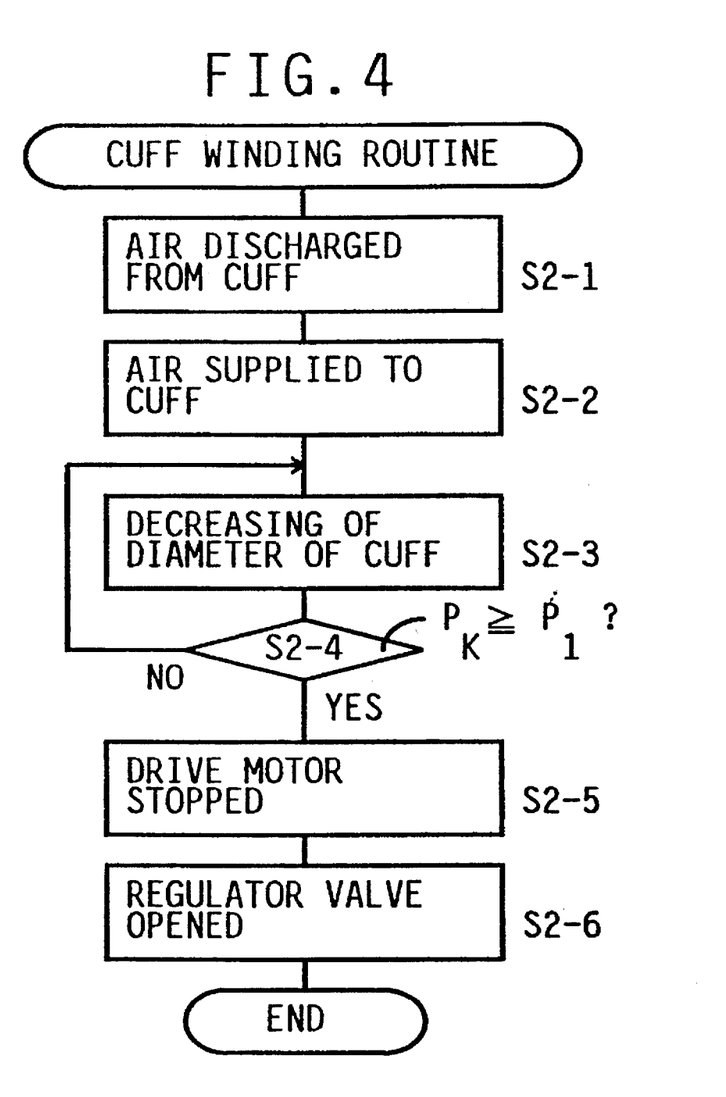
FIG. 4 is a flow chart representing a cuff winding routine of the control program of FIG. 3.

The cuff winding routine is illustrated in detail in the flow chart of FIG. 4. First, at Step S2-1, the air pump 18 is rotated in a reverse direction, so that the air in the bag 12 is discharged into ambient atmosphere and the volume of the bag 12 is reduced to a minimum. At the following Step S2-2, the air-deflation regulator valve 20 is closed and the air pump 18 is rotated in a normal direction (opposite to the reverse direction) for a predetermined time duration, so that a predetermined amount of air is supplied into the bag 12 of the cuff 10. This air is necessary to judge whether the belt 14 or cuff 10 is wound around the patient's upper arm in an appropriate manner. The amount of the air is pre-determined by experiments. Subsequently, at Step S2-3, the drive motor 48 is rotated in a normal direction so that the outer end 14b of the cylindrically bent belt 14 is pulled together with the movable member 54 which is moved by the endless belt 46 driven by the drive motor 48. Thus, the reduction of the diameter of winding of the belt 14 is started. At the following Step S2-4, the CPU 30 judges whether the pressing pressure Pk of the bag 12 has reached a reference value, P1. The reference pressure P1 is employed for judging whether the belt 14 or cuff 10 is wound around the patient's upper arm in an appropriate manner. The reference pressure P1 is pre-determined at 10 to 30 mmHg.

A negative judgment made at Step S2-4 indicates that the amount or length of pulling of the belt 14 is not enough, that is, that the diameter of winding of the belt 14 has not been sufficiently reduced yet. Therefore, the CPU 30 repeats Steps S2-3 and S2-4. Meanwhile, if a positive judgment is made at Step S2-4, the control of the CPU 30 proceeds with Step S2-5 to stop the normal-direction rotation of the drive motor 48 so as to hold a position of the cuff 10 relative to the patient's upper arm, more specifically, hold the belt 14 at a diameter of winding thereof at the time when the pressing pressure Pk of the bag 12 has reached the reference value P1 and therefore a positive judgment is made at Step S2-4. Since the drive motor 48 is associated with the reduction gears, the drive pulley 50 becomes immovable upon stopping of the drive motor 48. Thus, the belt 14 or cuff 10 is fixed to an appropriate position relative to the patient's upper arm. Subsequently, at Step S2-6, the CPU 30 opens the regulator valve 20 and reduces the pressure Pk of the bag 12 down to the atmospheric pressure.

Following the cuff winding routine at Step S2, the control of the CPU 30 goes to Step S3 to close the regulator valve 20 and operate the air pump 18 so as to supply a pressurized air into the bag 12 of the cuff 10 and thereby quickly increase the cuff pressure Pk. Step S3 is followed by Step S4 to judge whether the cuff pressure Pk has reached a target value, P2, at which the blood flow through the arteries under the cuff 10 is stopped. The target value P2 is pre-determined at, e.g., 180 mmHg higher than a systolic blood pressure of the patient.

If a negative judgment is made at Step S4, the CPU 30 repeats Steps S3 and S4. Meanwhile, if a positive judgment is made at Step S4, the control of the CPU 30 proceeds with Step S5 to stop the operation of the air pump 18 and change the degree of opening of the regulator valve 20 so as to slowly deflate the bag 12 of the cuff 10. This slow cuff deflation is carried out at a rate of 2 to 3 mmHg/sec, for example, that is suitable for BP measurement. Step S5 is followed by Step S6 to judge whether the CPU 30 has received a span of pulse wave signal SM corresponding to one pulse, i.e., one heartbeat of the patient. If a negative judgment is made at Step S6, the CPU 30 repeats Steps S5 and S6.

Meanwhile, if a positive judgment is made at Step S6, the control of the CPU 30 proceeds with Step S7 to execute a BP measuring routine according to a known oscillometric BP determination algorithm, i.e., determine the systolic and diastolic BP values of the patient. Step S7 is followed by Step S8 to judge whether the BP measuring routine at Step S7 has been completed. While the cuff pressure Pk is slowly decreased, the respective amplitudes of successive pulses of the pulse wave signal SM first increase and then decrease. The amplitude of each pulse is obtained by subtracting the lower-peak magnitude of the one-pulse signal SM from the upper-peak magnitude of the same. According to the known oscillometric BP determination algorithm, a cuff pressure Pk at the time when the pulse amplitudes significantly largely increase is determined as a systolic BP value, Psys, of the patient; a pressure Pk at the time of detection of the greatest pulse amplitude is determined as a mean BP value, Pmean; and a pressure Pk at the time when the pulse amplitudes significantly largely decrease is determined as a diastolic BP value, Pdia.

If a negative judgment is made at Step S8, the CPU 30 repeats Steps S5 through S8. Meanwhile, if a positive judgment is made at Step S8, the control of the CPU 30 proceeds with Step S9 to fully open the regulator valve 20 so as to quickly deflate the bag 12 of the cuff 10, i.e., quickly decrease the cuff pressure Pk. Concurrently, the CPU 30 rotates the drive motor 48 in a reverse direction (opposite to the normal direction) so as to increase the diameter of winding of the belt 14 and thereby release the patient's upper arm from the cuff pressure Pk. Step S9 is followed by Step S10 to store the three BP values Psys, Pmean, Pdia in the RAM 32 and display those BP values in digits on the image display of the output device 38.

In the present embodiment, Step S2-2 corresponds to the step of supplying a predetermined amount of gas into the inflatable chamber 12 of the cuff 10, and holding the gas in the chamber 12; Step S2-3 corresponds the step of increasing a tension of the cuff 10 so that the pressure Pk of the bag 12 of the cuff 10 reaches a reference value P1; and Step S2-5 corresponds to the step of fastening a position of the cuff 10 relative to the body portion of the subject.

Also, in the present embodiment, the air pump 18, regulator valve 20, and control device 28 cooperate with each other to serve as a gas supplying device which supplies a predetermined amount of gas into the chamber 12 of the cuff 10 and holds the gas in the chamber 12; the cuff winding device 40 corresponds to a driving device which increases a tension of the cuff 10 so as to reduce a diameter of winding of the cuff 10; Step S2-4 corresponds to judging means for judging whether the pressure Pk of the bag 12 of of the cuff 10 has reached a reference value P1; and when the judging means makes a positive judgment, the driving device holds the diameter of winding of the cuff 10.

As is apparent from the foregoing description, in the present embodiment, the control device 28 or CPU 30 operates the drive motor 48 of the cuff winding device 40, at the beginning of BP measurement, in such a way that the cuff 10 is automatically wound around the patient's upper arm in an appropriate manner. Thus, with the present apparatus, the cuff 10 is automatically and appropriately wound around the subject's body portion without requiring the skill of the user. Therefore, the present apparatus effectively prevents the accuracy of BP measurement from being lowered because of inappropriate winding of the cuff 10 around the subject's body portion, i.e., inappropriate pressing of the subject's body portion with the pressing pressure Pk.

The present BP measuring apparatus is of an oscillometric type wherein BP values are determined based on the respective amplitudes of successive pulses of a pulse wave detected as a pressure oscillation produced in the bag 12 of the cuff 10, and the detection of the pulse wave is free from adverse influence due to inappropriate winding of the cuff 10 around the subject's body portion. Thus, the accuracy of oscillometric BP measurements is increased to a higher level. Additionally, in the case where a medical diagnosis is made based on the waveform of pulse wave detected from the cuff 10, the accuracy of diagnosis is increased.

Figure 5:
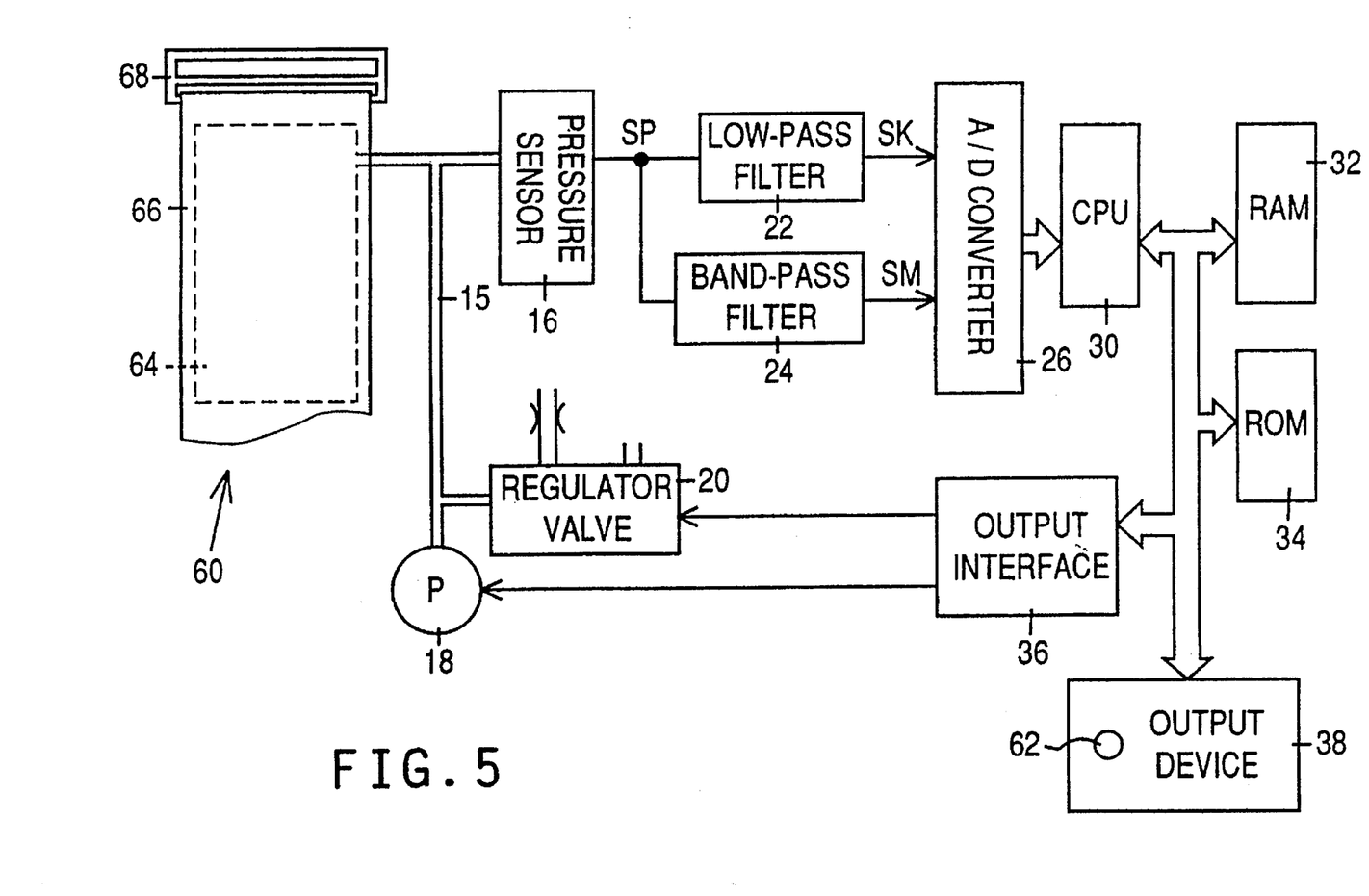
FIG. 5 is a diagrammatic view corresponding to FIG. 1, showing a second embodiment of the present invention.
Figure 6:
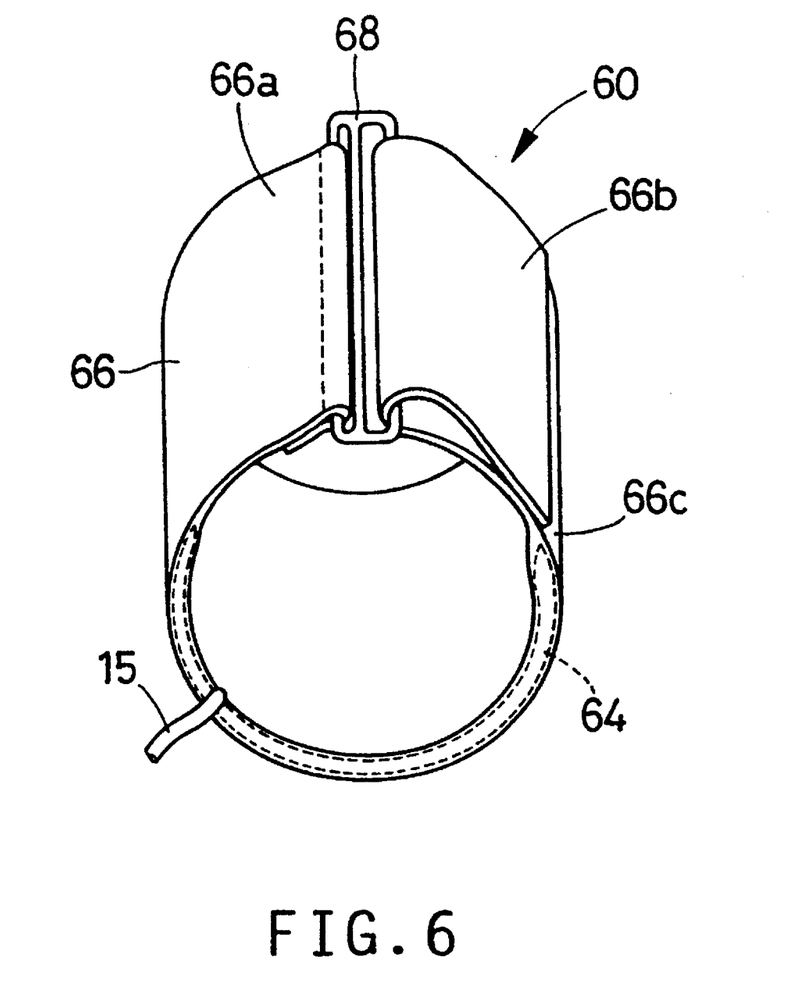
FIG. 6 is a perspective view of a cuff 60 of the apparatus of FIG. 5.
Figure 7:
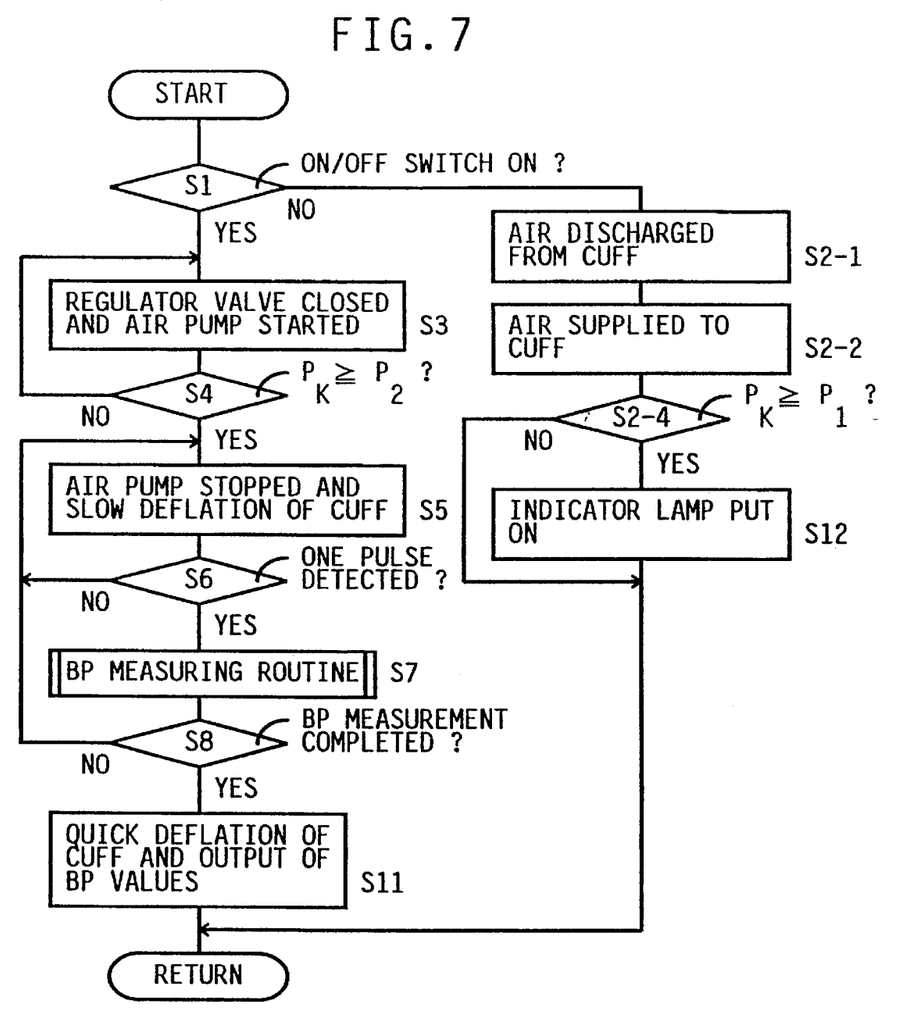
FIG. 7 is a flow chart representing a control program according to which the apparatus of FIG. 5 operates.

Referring next to FIGS. 5 through 7, there will be described the second embodiment of the present invention. The same reference numerals and symbols as used for the first embodiment shown in FIGS. 1 through 4 are used for designating the corresponding parts or steps for the second embodiment, and the description of those elements are omitted.

FIG. 5 shows an automatic BP measuring apparatus of a type wherein a user winds, using his or her hands, an inflatable cuff 60 around a body portion of a living subject. The second embodiment is different from the first embodiment of FIG. 1 in that the former does not have the drive motor 48 (or cuff winding device 40) and has an output device 38 additionally including an indicator lamp 62.

As shown in detail in FIG. 6, the cuff 60 includes (a) an elastically deformable bag 64 formed of rubber or vinyl; (b) an elongate cloth belt 66 accommodating the bag 64; and (c) a ring member 68 attached to one end 66a of the belt 66. After the user winds the cuff 60 around the body portion of the subject, he or she passes the other, free end 66b of the belt 66 through the ring member 68, and folds back the free end 66b of the belt 66 and detachably secures it to an outer surface 66c of the belt 66 with a fastener such as a pair of magic tapes (not shown) fixed to the free end 66b and the outer surface 66c, respectively.

There will be described the operation of the BP measuring apparatus of FIG. 5 by reference to the flow chart of FIG. 7 wherein Steps S1, S3—S8, S2-1, S2-2, and S2-4 are the same as those of the flow charts of FIGS. 3 and 4.

In the second embodiment, if a negative judgment is made at Step S1, the control of a CPU 30 goes to Step S2-1 to deflate the bag 64 of the cuff 60. Step S2-1 is followed by Step S2-2 to supply a predetermined amount of air into the bag 64 and hold the air in the bag 64. At the following Step S2-4, the CPU judges whether the pressing pressure Pk of the bag 64 has reached a reference value P1. If a negative judgment is made at Step S2-4, the CPU 30 repeats Steps S1, S2-1, S2-2, and S2-4. Meanwhile, if a positive judgment is made at Step S2-4, the control of the CPU 30 proceeds with Step S12 to light the indicator lamp 62 indicating that the cuff 60 is wound around subject's body portion in an appropriate manner. Until the lamp 62 is put on, the user continues to pull the free end 66b of the belt 66 through the ring member 68 so as to reduce the length of contact of the cuff 60 with the subject's body portion. When the lamp 62 is put on, the user secures the free end 66b of the belt 66 to the outer surface 66c of the belt by using the fastener, thus completing the winding of the cuff 60 around the body portion.

After the winding of the cuff 60 is completed as described above, the user operates an ON/OFF switch (not shown) to an "ON" position. Thus, a positive judgment is made at Step S1, and Steps S3 to S8 are carried out for a BP measurement in the same way as described for the first embodiment. After the BP measurement is completed and a positive judgment is made at Step S8, the control of the CPU 30 goes to Step S11 to quickly deflate the cuff 60 or bag 64 and output the BP values obtained at Step S7.

In the second embodiment, the air pump 18, regulator valve 20, CPU 30, Step S2-2, etc. cooperate with each other to provide a gas supplying device which supplies a predetermined amount of gas into the cuff 60 and holds the gas in the cuff 60. The indicator lamp 62, CPU 30, Step S12, etc. cooperate with each other to provide an indicating device which indicates that the cuff pressure Pk has reaches the reference value P1. The user can easily wind the cuff 60 around the subject's body portion in an appropriate manner, by pulling the cuff 60 until the lamp 62 is put on and subsequently fastening the cuff 60. Thus, the present BP measuring apparatus does not need the skill of a user, and effectively prevents the lowering of accuracy of a BP measurement resulting from an inappropriate winding of the cuff 60.

Figure 8:
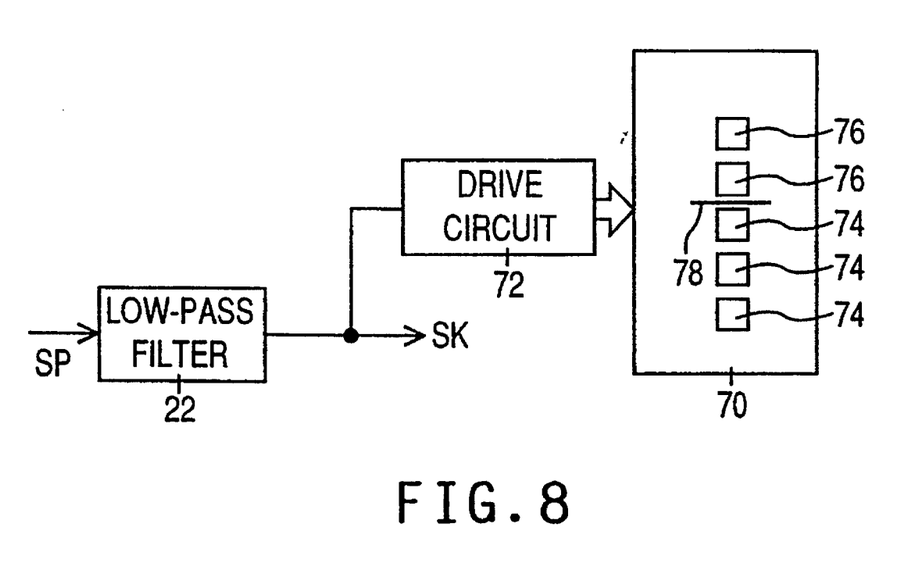
FIG. 8 is a perspective view of a pressure indicator employed in a third embodiment of the present invention.

FIG. 8 shows an indicating device which may be employed in place of the indicator lamp 62 used in the second embodiment. The indicating device has a pressure indicator 70 including three green light emitting diodes (LEDs) 74 and two red LEDs 76 which are arranged in a single array. As the cuff pressure Pk increases, a drive circuit 72 puts on one by one the green and red LEDs 74, 76 in a direction from bottom to top, thereby increasing the number of "ON" LEDs 74, 76. Similarly, as the cuff pressure Pk decreases, the drive circuit 72 puts off one by one the red and green LEDs 76, 74 in an opposite direction from top to bottom, thereby decreasing the number of "ON" LEDs 74, 76. The indicator 70 has a mark 78 at a position corresponding to a pressure equal to the reference value P1 employed in the second embodiment. While observing the pressure indicator 70, the user can easily wind the cuff 60 around the body portion in an appropriate manner. With this modification, the BP measuring apparatus enjoys the same advantages as described above for the second embodiment.

While the present invention has been described in its preferred embodiments, the present invention may otherwise be embodied.

For example, while in the illustrated embodiments Step S2-1 is provided before Step S2-2, it is possible to provide Step S2-1 following Step S10 of FIG. 3 or Step S11 of FIG. 7.

In the illustrated embodiments, the cuff 10, 60 includes the bag 12, 64 and the belt 14, 66 which are formed of different materials. However, it is possible to employ such a cuff (e.g., disposable cuff) which is constituted by two superposed vinyl sheets and has an air chamber formed by welding the two sheets.

At Step S2-2, the supplying of the predetermined amount of air into the cuff 10, 60 is effected by operating the air pump 18 for a predetermined time duration. However, in the case where the cuff 10, 60 is held to a predetermined three-dimensional position thereof, the same result may be achieved by operating the air pump 18 till the cuff pressure Pk detected by the pressure sensor 16 reaches a predetermined value.

For holding the predetermined amount of gas in the cuff 10, 60, it is possible to provide small springs inside the bag 12, 64 so that the cuff 10, 60 always has a volume corresponding to the predetermined amount of gas.

Although all the illustrated BP measuring apparatus are of the oscillometric type, the principle of the present invention is applicable to other types of BP measuring apparatus such as a Korotkoff-sound type wherein a systolic and a diastolic BP value are determined based on the first and last detection of Korotkoff sounds using a microphone.

In place of, or in addition to, the indicator lamp 62 or pressure indicator 70, it is possible to employ an alarming device which issues an alarm sound when the pressure Pk of the cuff 12, 64 reaches the reference value P1.

It is to be understood that the present invention may be embodied with other changes, improvements, and modifications that may occur to those skilled in the art without departing from the spirit and scope of the invention defined in the appended claims.

What is claimed is:

1. A method of winding a cuff having an inflatable chamber around a body portion of a living subject, in measuring a blood pressure of the subject, comprising the steps of:

positioning said cuff and said body portion of said subject relative to each other such that the cuff surrounds the body portion, supplying a predetermined amount of gas into said chamber of said cuff to hold said gas in said chamber, and fastening said cuff surrounding said body portion after increasing a tension of the cuff until a gas pressure in said chamber of the cuff in which said predetermined amount of gas is held reaches a reference value.

2. An apparatus for winding a cuff having an inflatable chamber around a body portion of a living subject, in measuring a blood pressure of the subject, the cuff and the body portion being positioned relative to each other such that the cuff surrounds the body portion, the apparatus comprising:

a gas supplying device which supplies a predetermined amount of gas into said chamber of said cuff to hold said gas in said chamber;

a pressure sensor which detects a gas pressure in said chamber of said cuff;

judging means for judging whether said gas pressure of said chamber detected by said pressure sensor has reached a reference value; and a driving device which increases a tension of said cuff to reduce a diameter of said cuff surrounding said body portion of said subject, said driving device holding said diameter of said cuff when said judging means makes a positive judgment that said gas pressure of said chamber of said cuff in which said predetermined amount of gas is held has reached said reference value.

3. A cuff winding apparatus according to claim 2, further comprising a support member which supports an inner end of said cuff which is bent to have a generally cylindrical shape so as to permit said body portion of said subject to be inserted into the cylindrical cuff.

4. A cuff winding apparatus according to claim 2, wherein said driving device comprises:

a movable member fixed to an outer end of said cuff which is bent to have a generally cylindrical shape so as to permit said body portion of said subject to be inserted into the cylindrical cuff;

a drive belt to which said movable member is fixed; and a drive motor which is selectively operable in a first state thereof in which said motor is rotated in a normal direction to move said drive belt and said movable member in a normal direction and thereby pull said outer end of said cuff, so as to reduce said diameter of the cuff surrounding said body portion of said subject, in a second state thereof in which said motor is stopped to stop the drive belt and the movable member and thereby hold the diameter of the cuff when said judging means makes said positive judgment, and in a third state thereof in which said motor is rotated in an opposite direction to allow the drive belt and the movable member to move in an opposite direction because of a restoring force of the cuff, so as to increase the diameter of the cuff surrounding the body portion of the subject.

5. A cuff winding apparatus according to claim 2, wherein said gas supplying device comprises:

an air pump which is selectively operable in a first state thereof in which said pump is rotated in a normal direction to supply a pressurized air into said chamber of said cuff and in a second state thereof in which the pump is rotated in an opposite direction to discharge said air from said chamber; and a regulator valve which is selectively operable in a closed position thereof in which said valve permits said air to be held in said chamber of said cuff and in an open position thereof in which the valve permits said air to be discharged from said chamber.

6. An apparatus for winding a cuff having an inflatable chamber around a body portion of a living subject, in measuring a blood pressure of the subject, the cuff and the body portion being positioned relative to each other such that the cuff surrounds the body portion, the apparatus comprising:

a gas supplying device which supplies a predetermined amount of gas into said chamber of said cuff to hold said gas in said chamber, said gas supplying device comprising an air pump which is selectively operable in a first state in which said pump is rotated in a normal direction to supply pressurized air into said chamber of said cuff and in a second state in which the pump is rotated in an opposite direction to discharge said air from said chamber, and a regulator valve which is selectively operable in a closed position in which said valve permits said air to be held in said chamber of said cuff and in an open position in which the valve permits said air to be discharged from said chamber;

a pressure sensor which detects a gas pressure in said chamber of said cuff; and an indicating device which indicates that said gas pressure of said chamber detected by said pressure sensor has reached a reference value while a tension of said cuff having said chamber in which said predetermined amount of gas is held and surrounding said body portion of said subject is being increased by a person.

7. A cuff winding apparatus according to claim 6, further comprising:

a ring member which is attached to one end of said cuff and through which the other end of said cuff is passed by said person so that the cuff surrounds said body portion of said subject; and a fastener which is attached to at least one of said other end of said cuff and an outer surface of the cuff and with which said other end of the cuff is secured by said person to said outer surface of the cuff when said indicating device indicates that said pressure of said chamber of the cuff has reached said reference pressure.

8. A cuff winding apparatus according to claim 6, wherein said indicating device comprises an indicator lamp which lights when said pressure of said chamber detected by said pressure sensor reaches said reference value.

9. A cuff winding apparatus according to claim 6, wherein said indicating device comprises a plurality of light emitting elements each of which lights when said pressure of said chamber detected by said pressure sensor reaches a corresponding one of a plurality of different pressure values, said reference value falling between a maximum and a minimum value of said different pressure values.

* * * * *